United States Patent
Bara

(10) Patent No.: US 6,565,862 B1
(45) Date of Patent: May 20, 2003

(54) MAKEUP OR CARE COMPOSITION COMPRISING A HYDROPHILIC ORGANOPOLYSILOXANE

(75) Inventor: Isabelle Bara, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/492,519

(22) Filed: Jan. 27, 2000

(30) Foreign Application Priority Data

Jan. 28, 1999 (FR) .............................. 99 00957

(51) Int. Cl.$^7$ .............................. A61K 7/42; A61K 7/04; A61K 7/021; A61K 7/025; A61K 7/32

(52) U.S. Cl. ........................... 424/401; 424/59; 424/61; 424/63; 424/64; 424/65; 424/70.1; 424/70.7; 424/70.12; 424/400; 424/401

(58) Field of Search ................. 424/400, 401, 424/59, 61, 63, 64, 65, 70.1, 70.7, 70.12

(56) References Cited

U.S. PATENT DOCUMENTS

| | | | |
|---|---|---|---|
| 5,412,004 A | | 5/1995 | Tachibana et al. |
| 5,599,533 A | | 2/1997 | Stepniewski et al. |
| 5,616,598 A | | 4/1997 | Lion et al. |
| 5,833,973 A | | 11/1998 | Dobkowski et al. |
| 5,928,660 A | | 7/1999 | Kobayashi et al. |
| 6,117,933 A | * | 9/2000 | Ozaki et al. ................. 524/503 |

FOREIGN PATENT DOCUMENTS

| | | |
|---|---|---|
| EP | 0 848 029 | 6/1988 |
| EP | 0 295 886 | 12/1988 |
| EP | 0 381 166 | 8/1990 |
| EP | 0 602 905 | 6/1994 |
| EP | 0 667 146 | 8/1995 |
| EP | 0 687 461 | 12/1995 |
| EP | 0 707 083 | 4/1996 |
| EP | 0 790 055 | 8/1997 |
| EP | 0 855 178 | 7/1998 |
| FR | 2 650 890 | 2/1991 |
| JP | 61-65809 | 4/1986 |
| JP | 62-61911 | 3/1987 |
| JP | 2-295912 | 12/1990 |
| JP | 10-175816 | 6/1998 |
| WO | WO 97/44010 | 11/1997 |
| WO | WO 98/00105 | 1/1998 |

* cited by examiner

*Primary Examiner*—Jose' G. Dees
*Assistant Examiner*—Marina Lamm
(74) *Attorney, Agent, or Firm*—Finnegan, Henderson, Farabow, Garrett & Dunner, LLP

(57) ABSTRACT

A transfer-resistant, mattifying composition comprising, as a thickener, particles of an at least partially crosslinked elastomeric solid organopolysiloxane in suspension in an aqueous phase. The composition is more particularly a composition for caring for or making up the lips, or a foundation composition for making up both the human face and the human body. The composition is soft and fresh on application, spreads easily, is nonsticky, and does not dry out the skin or lips. It is perfectly suited to greasy skin because of its high mattifying power.

26 Claims, No Drawings

MAKEUP OR CARE COMPOSITION COMPRISING A HYDROPHILIC ORGANOPOLYSILOXANE

The present invention relates to a transfer-resistant cosmetic composition for caring for and/or making up human hair, skin, nails, and/or lips, which imparts both mattifying and freshness properties. In particular, the invention relates to a lip composition, e.g., a lipstick, an eyeliner, a face powder, an eyeshadow, a foundation, an antisun product, a deodorant, or a treating shampoo, which may be in the form of an aqueous gel, lotion, or cream, or cast as a stick or as a disk.

By "mattifying" is meant the creation of a matte effect or finish. A matte effect is particularly desired for users with combination or greasy skin, in particular in hot and humid climates. Mattifying fillers are generally absorbent fillers, such as talc, silica or kaolin, or fillers exhibiting light scattering optical properties, which properties are referred to as a "soft-focus effect".

Lip and foundation compositions according to the prior art generally comprise fatty substances, such as oils, pasty compounds and waxes, and a particulate phase which is generally composed of fillers and pigments. The fillers generally serve to modify the texture of the composition and to mattify the film or layer of composition deposited on the skin and/or lips, whereas the pigments are generally used to contribute color to the composition. Recently, use has been made of mattifying polymers (see, for example, European patent application EP-A-790,055), such as crosslinked silicone polymers known under the commercial references KSG (KSG 6, 16, 17 and 18) from the company Shin Etsu, Tréfils from the company Dow Corning, or Gransils from the company Grand Industrie.

(KSG 6, 16, 17 and 18) from the company Shin Etsu, Tréfils from the company Dow Corning, or Gransils from the company Grand Industrie.

The disadvantage of these commercial products is that they comprise linear or cyclic silicone oils of the non-crosslinked polydimethylsiloxanes (PDMS) type and that they contribute an oily and greasy effect, without a fresh effect, which does not allow them to be used, or allows them to be used with difficulty, in a hot and humid environment by users with greasy skin. Furthermore, these commercial products, even those devoid of silicone oil, Tréfils 505 C from Dow Dorning, for example, are difficult to disperse in an aqueous medium. These products are presented as "water-insoluble" elastomeric silicone polymers. See in particular the European patent application in the name of Kao, EP-A-0,855,178.

These polymers, which are difficult to incorporate in an aqueous phase, are completely water repellent. Due to their high incompatibility with water, and in particular with sweat, the latter is not absorbed by these polymers and even has a tendency to "pearl" at the surface of the skin during perspiration. The mattifying effect of these polymers, therefore, has a tendency to fade over time. Recently, emulsions comprising this type of polymer have been devised (see, for example, U.S. Pat. No. 5,412,004, to Tachibana, et al., and U.S. Pat. No. 5,599,533, to Stepniewski, et al.) for the purpose of improving their cosmetic properties. These stable emulsions, although contributing less greasiness and more freshness than anhydrous products, also lose the mattifying property initially contributed by the crosslinked silicone polymers.

There exist compounds of the crosslinked organosiloxane type which disperse in aqueous media, such as, for example, the compounds of KSG 20 or KSG 21 type sold by the company Shin Etsu. It is the specific chemical structure of these compounds which is responsible for this dispersion in aqueous medium, i.e., the presence of polar groups conferring surface-active properties on them. However, these known compounds, in contrast to those of the composition of the invention, do not contribute the desired matte effect.

Furthermore, known foundation and/or lip compositions, when they are applied to the skin or lips, exhibit the disadvantage of transferring. By "transferring", it is meant that the composition is at least partly deposited, leaving marks on certain surfaces with which the applied composition may be brought into contact, such as, for example, a glass, a cup, a cigarette, an item of clothing, or the skin. This results in a mediocre persistence of the applied film on the skin or lips, requiring regular renewal of the application of the foundation or lip composition by the user. Furthermore, the appearance of these unacceptable marks, in particular on blouse collars, can dissuade some women from using this type of makeup composition.

As a result, cosmetic scientists have been interested in "transfer-free" lip and foundation compositions for several years. By "transfer-free", or "transfer-resistant", it is meant a composition, in particular a cosmetic composition, which transfers little or not at all. Thus, the company Shiseido has envisaged, in its Japanese patent application JP-A-61-65809, "transfer-free" lip compositions comprising from 1 to 70% by weight of a siloxysilicate resin (with a three-dimensional network) comprising pendant alkyl chains comprising from 1 to 6 carbon atoms or pendant phenyl chains, from 10 to 98% by weight of a volatile silicone oil with a cyclic silicone chain, and pulverulent fillers. Likewise, the company Noevier has disclosed, in its Japanese patent application JP-A-62-61911, "transfer-free" lip compositions, eyeliner, and foundation compositions comprising one or more volatile silicones in combination with one or more hydrocarbonaceous waxes.

More recently, the company Revlon has envisaged, in its European patent application EP-A-602,905, "transfer-free" lip compositions comprising a cyclic or linear volatile silicone with pendant methyl chains, and a silicone resin comprising a pendant ester chain having from 12 to 18 carbon atoms. However, the lip film remaining on the lips after evaporation of the volatile silicone has the disadvantage of lacking comfort on application, and in particular of being too dry. In addition, Revlon has envisaged, in its European patent application EP-A-709,083, "transfer-free" foundations comprising a volatile silicone in combination with a siloxysilicate resin. These foundations also exhibit the disadvantage of not being very comfortable and of being dry over time.

These compositions, although entirely satisfactory with regard to the "transfer-free" property, exhibit the disadvantage of leaving on the lips, after evaporation of the silicone oils, a film which becomes uncomfortable over time (feeling of dryness and tightness), thus dissuading a number of women from using this type of makeup product. To improve the comfort of this type of composition, it might be possible to add nonvolatile oils, but, in this case, there would be a loss in "transfer-free" effectiveness.

Accordingly, the need remains for a mattifying composition with properties which persist on the skin over time, i.e., have little or no transferability, and which at the same time contribute properties of freshness.

A subject of the present invention, therefore, is a care or makeup composition which makes it possible to overcome the various disadvantages set forth above, and which makes it possible in particular to obtain a film which does not transfer, which composition exhibits improved cosmetic properties with respect to those of the "transfer-free" products of the prior art, in particular the properties of slip or ease of application, of nontightness and of nondryness of the lips, and mattifying and freshness properties which are superior to those of the mattifying products of the prior art. The invention applies not only to products for making up human lips and skin, but also to products for caring for and/or for treating human lips and skin. The composition of the invention can also be applied to the hair and scalp.

Thus, a subject of the invention is a mattifying and/or transfer-resistant composition for making up or caring for keratinous materials, including the hair, skin, nails, and lips, comprising, as a thickener, particles of an at least partially crosslinked elastomeric solid organopolysiloxane in suspension in an aqueous phase. The term "elastomeric" is understood to mean a flexible and deformable material having viscoelastic properties, and in particular the consistency of a sponge or of a flexible sphere. Its modulus of elasticity is such that this material is resistant to deformation and has a limited ability to expand and to contract. This material is capable of returning to its original shape after it has been stretched. This elastomer is formed of polymeric chains of high molecular weight, the mobility of which is limited by a uniform network of crosslinking points.

The elastomeric organopolysiloxanes of the composition of the invention exhibit aqueous medium structuring properties, and are capable of increasing the viscosity of the aqueous phase. They do not dry the skin, but do contribute good cosmetic properties to the composition, in particular the properties of softness, freshness, matteness and transfer-resistance. These novel elastomers result in compositions which are comfortable on application, spread well, i.e., have good slip, are soft, and are not sticky to the touch. These cosmetic properties are due, on the one hand, to the texture of the organopolysiloxanes, and, on the other hand, to their properties, comparable to those of microsponges, of trapping aqueous media and in particular those of the composition and those due to perspiration of the skin.

The composition of the invention can be provided in the form of a paste, a solid, or a more or less fluid cream. It can also be a more or less fluid oil-in-water or water-in-oil emulsion, or a solid or soft hydrophilic gel. This composition can have the appearance of a lotion, a gel, a cream, or a cast product, and can even be provided in the form of an aerosol.

The elastomeric organopolysiloxanes useful in accordance with the invention are hydrophilic compounds which are partially or completely crosslinked and have a three-dimensional structure. The aqueous phase can be completely or partially thickened by these elastomers.

The elastomers of the invention are provided in the form of a powder or gel which is emulsified forming an elastomeric organopolysiloxane with a three-dimensional structure dispersed in water. The dispersion (or suspension) of the particles is homogeneous.

The elastomeric organopolysiloxanes according to the invention can be chosen from the crosslinked polymers disclosed in Japanese patent application JP-A-10/175816, the disclosure of which is incorporated herein by reference. According to this application, they are obtained by an addition and crosslinking reaction, in the presence of a catalyst, in particular of the platinum type, of at least (i) one organopolysiloxane having at least two vinyl groups in the $\alpha,\omega$-positions of the silicone chain per molecule, and (ii) one organopolysiloxane having at least one hydrogen atom bonded to a silicon atom per molecule.

In particular, the organopolysiloxane (i) is chosen from polydimethylsiloxanes and is more specifically an $\alpha,\omega$-dimethylvinylpolydimethylsiloxane.

The elastomeric organopolysiloxanes of the composition according to the invention are advantageously provided in the form of an aqueous suspension. This suspension can be obtained, in particular, as follows:

(a) mixing the organopolysiloxane (i) and the organopolysiloxane (ii);

(b) adding the aqueous phase comprising an emulsifier to the mixture of step (a);

(c) emulsifying the aqueous phase and the mixture;

(d) adding hot water to the emulsion of step (c); and (e) polymerizing the organopolysiloxane (i) and the organopolysiloxane (ii) as an emulsion in the presence of a platinum catalyst.

The water is advantageously added at a temperature of 40–60° C. After step (e), it is possible to dry the particles obtained, in order to evaporate therefrom all or part of the trapped water.

The organopolysiloxanes are in the form of hydrophilic deformable solid particles having a degree of hardness measurable with a Shore A durometer (according to ASTM Standard D2240) at room temperature or with the Japanese method JIS-A. The hardness can be measured on an elastomer block prepared for this purpose as follows: (1) mixing the organopolysiloxane (i) and the organopolysiloxane (ii); (2) removing the air from the mixture; (3) molding and vulcanizing the mixture in an oven at 100° C. for 30 minutes; and (4) cooling the elastomer block to room temperature and then measuring its hardness. The relative density can also be determined on this elastomer block.

In particular, the JIS-A hardness is less than or equal to 80, and better still, less than 65. The organopolysiloxanes of the composition of the invention can be, for example, those sold under the names BY 29-122 and BY 29-119 by the company Dow Corning Electric. An elastomer block according to the product BY 29-122 exhibits a hardness of JIS-A 7, and an elastomer block according to the product BY 29-119 exhibits a hardness of 30. The relative density ranges from 0.97 to 0.98. It is also possible to use a mixture of these commercial products.

The elastomeric organopolysiloxane (as active material) particles have a size ranging from 0.1 to 500 $\mu$m, and better still, from 3 to 200 $\mu$m. These particles can be spherical, flat, or amorphous, with preferably a spherical shape.

The elastomeric organopolysiloxane powder is preferably present in the composition in an amount of from 1 to 99%, and better still of from 5 to 70%. This corresponds to an amount of polymer, as active material, of from 0.5 to 65% by weight, and better still of from 3 to 45%. In fact, it acts as a water-dispersible filler.

These organopolysiloxane particles, in order to disperse in a stable way in water, can be used in combination with one or more nonionic, cationic or anionic surfactants with an HLB$\geq$8. Step (c) is preferably obtained in the presence of a nonionic emulsifier.

The proportion of surfactants is preferably from 0.1 to 20 parts by weight per 100 parts by weight of the elastomeric organopolysiloxane composition, and better still from 0.5 to 10 parts by weight. See, e.g., JP-A-10/175816.

Fatty substances known as oils, which are liquid at room temperature, such as those disclosed in JP-A-10/175816, waxes or gums which are solid at room temperature, pasty fatty substances of animal, vegetable, mineral, or synthetic origin, their mixtures, and inorganic powders such as those disclosed in this document, can be used in combination with these elastomeric organopolysiloxane powders. There is no limitation on the additional fatty phase, and it can comprise products which are fluid at room temperature, such as silicone oils, fluorinated oils, fluorosilicone oils, or hydrocarbonaceous oils which are optionally partially siliconated. These oils may be volatile at room temperature and atmospheric pressure. The term "volatile oil" is understood to mean in particular an oil which can evaporate in less than one hour on contact with the skin or lips. These oils can represent from 0 to 80% of the total weight of the composition.

Mention may in particular be made, as oils which can be used in the composition, of hydrocarbonaceous oils of animal origin, such as perhydrosqualene, vegetable hydrocarbonaceous oils such as liquid fatty acid triglycerides, for example sunflower, maize, soybean, gourd, grape seed, sesame, hazelnut, apricot, macadamia, castor, or avocado oils, or triglycerides of caprylic/capric acids such as those sold by the company Stéarineries Dubois or those sold under the names Miglyol 810, 812, and 818 by the company Dynamit Nobel, oils of formula $R^1COOR^2$ in which $R^1$ represents the residue of a higher fatty acid comprising from 7 to 19 carbon atoms and $R^2$ represents a branched hydrocarbonaceous chain comprising from 3 to 20 carbon atoms, such as, for example, purcellin oil, linear or branched hydrocarbons of mineral or synthetic origin such as volatile or nonvolatile liquid paraffins and their derivatives, liquid petrolatum, polydecenes, or hydrogenated polyisobutene such as parleam, synthetic esters and ethers such as isopropyl myristate or octanates, decanoates, or ricinoleates of alcohols or of polyalcohols, fatty alcohols such as octyldodecanol or oleyl alcohol, partially hydrocarbonaceous and/or siliconated fluorinated oils such as those disclosed in Japanese patent application JP-A-2-295912, the disclosure of which is incorporated herein by reference, silicone oils such as polymethylsiloxanes with a linear or cyclic silicone chain which are liquid or pasty at room temperature, phenyl dimethicones, phenyl trimethicones, polymethylphenylsiloxanes, and mixtures thereof.

The composition according to the invention can advantageously comprise hydrocarbonaceous, fluorinated, or silicone waxes, or their mixtures, which can be solid or semi-solid (i.e., in the form of a paste) at room temperature. These waxes can be of vegetable, mineral, animal, and/or synthetic origin. These waxes exhibit in particular a melting temperature of greater than 250° C., and better still of greater than 45° C.

The silicone waxes can be waxes comprising a silicone structure and units with one or more pendant alkyl or alkoxy chains and/or one or more alkyl or alkoxy chains at the end of the silicone structure, these chains being linear or branched and comprising from 10 to 45 carbon atoms. These waxes are known respectively as alkyl dimethicones and alkoxy dimethicones. Furthermore, these alkyl chains can comprise one or more ester functional groups. Mention may also be made, as additional waxes which can be used in accordance with the invention, of waxes of animal origin such as lanolin or beeswax, waxes of vegetable origin such as carnauba or candelilla wax, waxes of mineral origin such as paraffin wax, lignite wax, microcrystalline waxes, ceresin, or ozocerite, synthetic waxes such as polyethylene waxes, and mixtures thereof.

The presence of waxes in the compositions of the invention makes it possible to provide good mechanical strength, in particular when the composition is provided in the form of a stick. The composition can comprise from 0 to 50% of the total weight of the composition of wax, and preferably from 10 to 30%. These fatty substances should be chosen appropriately by a person skilled in the art in order to prepare a composition having the desired properties, for example, consistency and/or texture.

Moreover, the composition of the invention can comprise at least one additional ingredient conventionally used in the field, chosen from antioxidants, essential oils, preservatives, cosmetic or dermatological active principles, such as moisturizers (glycerol), vitamins, essential fatty acids, lipophilic sunscreens, fat-soluble polymers, in particular hydrocarbonaceous polymers such as polyalkylenes, gelling agents for the aqueous phase, gelling agents for the fatty phase, fragrances, surfactants, and mixtures thereof. These additional ingredients can be present in the composition according to the amounts conventionally used, for example in an amount of from 0 to 20% of the total weight of the composition, and better still of from 0.1 to 10%.

The composition of the invention advantageously comprises, as an additional ingredient, one or more gelling agents for the aqueous phase. Mention may be made among the gelling agents for the aqueous phase which can be used according to the invention of water-soluble cellulose gelling agents such as hydroxyethylcellulose, methylcellulose, hydroxypropylcellulose, and carboxymethylcellulose, guar gum, quaternized guar gum, nonionic guar gums comprising $C_1$–$C_6$ hydroxyalkyl groups, xanthan, locust bean, scleroglucan, gellan, rhamsan, or karoya gums, alginates, maltodextrin, starch and its derivatives, hyaluronic acid and its salts, clays such as montmorillonites, hectorites, bentones, or laponites, polymers with a carboxyl group such as crosslinked polyacrylic acids which are at least partially neutralized, for example, "Carbopol" or "Carbomer" products from the company Goodrich (Carbomer 980, for example, neutralized with triethanolamine, abbreviated TEA), poly(glyceryl (meth)acrylate) polymers, polyvinylpyrrolidone, poly(vinyl alcohol), crosslinked acrylamide polymers and copolymers, crosslinked methacryloyloxyethyltrimethylammonium chloride homopolymers, associative polyurethanes, and mixtures thereof. According to the invention, the gelling agent for the aqueous phase is preferably chosen from xanthan gum, clays (bentone or laponite), associative polyurethanes, cellulose thickeners, in particular hydroxyethyl cellulose, crosslinked polyacrylic acids which are at least partially neutralized, and mixtures thereof.

Of course, a person skilled in the art will take care to choose the optional supplementary additional ingredients and/or their amounts, so that the advantageous properties of the composition according to the invention are not, or not substantially, detrimentally affected by the envisaged addition. In particular, these additives must not be harmful to the homogeneity, the stability, the comfort, the matteness, the freshness, or the "transfer-free" properties of the composition.

The composition according to the invention can be provided in the form of a colored product, in particular for making up the skin, especially a foundation, a face powder, an eyeshadow, a mascara, an eyeliner, a concealer stick, or a nail varnish, or a lip composition for making up the lips, such as a lipstick. They can also be provided in uncolored form, optionally comprising cosmetic or dermatological active principles. They can then be used as a care base for the lips (for example, lip balms, protecting the lips from the cold and/or the sun and/or the wind), or a fixing base to be applied with a conventional lip composition. The fixing base then forms a protective film on the lip film of color, which limits the transfer thereof.

The composition of the invention can also be provided in the form of a dermatological or cosmetic composition for treating or caring for the hair, skin (including the scalp), nails, or lips, or in the form of a composition for antisun protection or artificial tanning, or in the form of a product for cleansing or removing makeup from the skin or keratinous fibers, a deodorant product, or a scenting product.

Of course, the composition of the invention must be cosmetically or dermatologically acceptable, namely non-toxic and capable of being applied to human skin, including the inside of the eyelids, or lips.

Preferably, the composition of the invention can comprise a coloring material comprising in particular a particulate phase which is generally present in an amount of from 0 to60% of the total weight of the composition, preferably of from 5 to 35%, and which can comprise pigments, pearlescent agents, fillers, or any mixture thereof, commonly used in cosmetic compositions, or colorants which are soluble in the medium, in particular water-soluble or fat-soluble colorants.

The term "pigments" should be understood as meaning white or colored, inorganic or organic particles, insoluble in the medium of the composition, intended to color and/or opacity the composition. The term "fillers" should be understood as meaning colorless or white, inorganic or synthetic, and lamellar or nonlamellar particles. The term "pearlescent agents" should be understood as meaning iridescent particles produced, in particular, by certain mollusks in their shells, or else synthesized. The fillers and pearlescent agents are used to modify the texture of the composition and the matteness/gloss effect.

The pigments can be present in the composition in an amount ranging from 0 to 60% of the weight of the final composition, and preferably from 4 to 25%. Mention may be made, as inorganic pigments which can be used in the invention, of titanium, zirconium, or cerium oxides, zinc, iron, or chromium oxides, and ferric blue. Mention may be made, among the organic pigments which can be used in the invention, of carbon black and barium, strontium, calcium, or aluminum lakes, and mixtures thereof.

The pearlescent agents can be present in the composition in an amount ranging from 0 to 20% of the total weight of the composition, preferably from 2 to 15%. Mention may be made, among the pearlescent agents which can be used in the invention, of mica covered with titanium oxide, with iron oxide, with natural pigment, or with bismuth oxychloride, such as colored titanium oxide-coated mica.

The fillers can be present in an amount ranging from 0 to 35% of the total weight of the composition, preferably from 5 to 15%. Mention may be made, in particular, of talc, mica, silica, kaolin, powders formed of Nylon® (Orgasol®, in particular, from Atochem) and of polyethylene, Teflon®, starch, boron nitride, microspheres formed of copolymers, such as Expancel® (Nobel Industrie) or Polytrap® (Dow Corning), and silicone resin microbeads (Tospearl® from Toshiba, for example), and mixtures thereof.

The water-soluble colorants are, for example, beet juice or methylene blue, and can represent from 0 to 6% of the total weight of the composition.

The composition according to the invention can be manufactured under cold conditions or by heating one or more elastomeric organopolysiloxanes in the form of a powder dispersed in water, addition of one or more pigments, of one or more fillers and/or of one or more other additives, optional addition of the fatty phase in the liquid state (in particular brought to the highest melting temperature of the waxes), and then emulsification, if necessary.

It can alternatively be obtained by extrusion as disclosed in European patent application EP-A-667,146, the disclosure of which is incorporated herein by reference. This process involves kneading the paste (waxes+oils+additives+pigments) during the cooling in order to create, in the body of the material, regions in which the paste is crushed using a roll mill or a screw extruder-mixer. This process makes it possible to obtain a composition in the form of a soft paste.

Another subject of the invention is the use of at least partially crosslinked elastomeric solid organopolysiloxane particles in suspension in an aqueous phase in a cosmetic composition for increasing the stability of the composition, and/or for increasing its freshness and/or matteness and/or softness and/or viscosity, and/or for decreasing the transfer of the composition and/or the deposition of marks on a surface brought into contact with the composition, after it has dried, and/or for mattifying keratinous substances.

Another subject of the invention is a process for increasing the freshness, matteness, stability, softness, viscosity of a cosmetic composition, and/or for decreasing the transfer of the composition, the process comprising introducing into the composition particles as defined above, of an at least partially crosslinked elastomeric organopolysiloxane in suspension in an aqueous phase.

The invention is illustrated in more detail in the following non-limiting examples. The percentages are given by weight.

EXAMPLE 1

| Creating a mattifying gel | |
| --- | --- |
| Carbomer 980 | 0.3% |
| TEA | 0.3% |
| Silicone BY 29-119 | 15% |
| Preservative | q.s. |
| Water | q.s. for 100% |

Result

Production of a highly mattifying gel with great freshness on application and good hold over time, and which retained a matte effect over time, in contrast to the products of the prior art.

Preparation

The organopolysiloxane was added to the water at room temperature, the gelling agent, the neutralizing agent, and the preservatives were subsequently added, and all the ingredients were then mixed with stirring.

EXAMPLE 2

| Creating a matte and fresh foundation | |
| --- | --- |
| Silicone BY 29-122 | 70% |
| Pigments (iron oxide) | 7% |
| Talc | 10% |
| Glycerol | 5% |
| Preservative | q.s. |
| Water | q.s. for 100% |

Result

Production of a fresh and very matte foundation with good hold over time.

Preparation

This composition was prepared as in Example 1.

EXAMPLE 3

Comparison of the mattifying effect of the hydrophilic organopolysiloxane (BY29-119) in aqueous dispersion with respect to a lipophilic organopolysiloxane (KSG-16) in oily dispersion.

This comparative test was carried out on 28 women with greasy and shiny skin on the forehead on half the face (a treated region of the forehead in contrast to an untreated region). The shininess of the skin was measured using a device of the Matidiag SEI-M-0029-MATI01 type, as disclosed in French patent application FR-A-2,650,890, the disclosure of which is incorporated herein by reference. The measurements were made at time T0, T10 minutes, T1 hour and T3 hours.

| Treatments | T10 minutes-T0 | T1 hour-T0 | T3 hours-T0 |
|---|---|---|---|
| BY-29-119 | −39% | −36% | −29% |
| KSG 16 | −19% | −17% | −14% |

It is clear from this table that the hydrophilic organopolysiloxane conferred a mattifying appearance which was significantly better than that of the lipophilic organopolysiloxane. This superiority was even apparent to a significant extent to the naked eye. This was because the product had a greater mattifying effect as the measured value became more negative. In addition, this matteness exhibited good hold over time.

EXAMPLE 4

Comparative Example

| Foundation according to the invention | |
|---|---|
| Titanium oxide (untreated anatase) | 6.48% |
| Amylopectin/amylose crosslinked with epichlorohydrin | 2.5% |
| Yellow iron oxide | 1.07% |
| Brown, yellow iron oxides | 0.3% |
| Black iron oxide | 0.15% |
| Sterilized demineralized water | 20% |
| Talc | 2.5% |
| Glycerol | 4% |
| Treated nanotitanium oxide as a 40% dispersion in water | 14% |
| Propylene glycol | 8% |
| Oxyethylenated polydimethylsiloxane comprising phosphate groups (MW*: 4500) | 1% |
| Crosslinked polydimethylsiloxane in dispersion in water/nonionic emulsifier (BY-29-119) | 40% |

*MW: weight-average molecular weight.

| Comparative foundation | |
|---|---|
| Titanium oxide (untreated anatase) | 6.48% |
| Yellow iron oxide | 1.07% |
| Brown, yellow iron oxides | 0.3% |
| Black iron oxide | 0.15% |

-continued

| Comparative foundation | |
|---|---|
| Mixture of crosslinked polydimethylsiloxane and of cyclopentadimethylsiloxane (6/94) (KSG 15 from Shin Etsu) | 92% |

The difference in amount of organopolysiloxane between the inventive and the comparative compositions was related to the feasibility of the compositions.

The inventive composition and the comparative composition were applied to women on half the neck (bare skin and treated skin), a moisturizing cream (Hydrative from Lancôme) having been applied beforehand. After drying in the air for 10 minutes, a cloth collaret was applied for 30 minutes. The deposit left on the collaret was subsequently observed with the naked eye. Grades from 0 to 7 were attributed to the deposit; the higher the grade, the more the composition transferred onto the collaret.

The inventive composition of example 4 received a mean grade of 3.8, and the comparative composition received a grade of 4.3. This difference was significant.

Furthermore, the uptake with a sponge of the inventive composition and its application to the skin were better than those of the comparative composition of this comparative example.

What is claimed is:

1. A solid composition for making up or caring for keratinous materials, comprising, as a thickener, an amount of particles of an at least partially crosslinked elastomeric solid organopolysiloxane in suspension in an aqueous phase that imparts mattifying or transfer-resistance properties to the composition, wherein from 5 to 60% of the total weight of the composition comprises a particulate phase containing pigments, pearlescent agents, fillers, and mixtures thereof.

2. A composition according to claim 1, wherein the at least partially crosslinked elastomeric solid organopolysiloxane particles are obtained by an addition and crosslinking reaction, in the presence of a catalyst, of at least (i) one organopolysiloxane having at least two vinyl groups in the α- and ω-positions of the silicone chain per molecule, and (ii) one organopolysiloxane having at least one hydrogen atom bonded to a silicon atom per molecule.

3. A composition according to claim 2, wherein the suspension of organopolysiloxane particles is obtained by:

(a) mixing the organopolysiloxane (i) and the organopolysiloxane (ii);

(b) adding the aqueous phase comprising an emulsifier to the mixture obtained in (a);

(c) emulsifying the aqueous phase and the mixture to obtain an emulsion;

(d) adding hot water to the emulsion of (c); and (e) polymerizing the organopolysiloxane (i) and the organopolysiloxane (ii) as an emulsion in the presence of a platinum-catalyst.

4. A composition according to claim 2, wherein the organopolysiloxane (i) is chosen from polydimethylsiloxanes.

5. A composition according to claim 4, wherein the organopolysiloxane (i) is an α,ω-dimethylvinylpolydimethylsiloxane.

6. A composition according to claim 3, wherein the polymerised emulsion is dried.

7. A composition according to claim 3, wherein said emulsifying is carried out with a non-ionic emulsifier.

8. A composition according to claim 1, wherein the particles have a size ranging from 0.1 to 500 µm.

9. A composition according to claim 8, wherein the particles have a size ranging from 3 to 200 µm.

10. A composition according to claim 1, wherein the organopolysiloxane particles exhibit a hardness of less than or equal to 80.

11. A composition according to claim 10, wherein the organopolysiloxane particles exhibit a hardness of less than or equal to 65.

12. A composition according to claim 1, additionally comprising a fatty phase.

13. A composition according to claim 11, wherein the fatty phase comprises at least one fatty substance chosen from volatile or nonvolatile oils; waxes, gums, and pasty fatty substances of animal, vegetable, mineral or synthetic origin, and mixtures thereof.

14. A composition according to claim 1, additionally comprising a gelling agent for the aqueous phase.

15. A composition according to claim 14, wherein the gelling agent for the aqueous phase is chosen from xanthan gum, clays, associative polyurethanes, cellulose thickeners, crosslinked polyacrylic acids which are at least partially neutralized, and mixtures thereof.

16. A composition according to claim 1, wherein the particulate phase is present in an amount ranging from 5 to 35% of the total weight of the composition.

17. A composition according to claim 1, additionally comprising at least one cosmetic or dermatological active principle.

18. A composition according to claim 1, wherein the composition is a foundation, a face powder, an eyeshadow, a concealer, a lip composition, an eyeliner, a mascara, a nail varnish, a care base, a fixing base for the lips, a dermatological or care product for the skin or keratinous fibers, a composition for antisun protection or artificial tanning, a product for cleansing the skin or keratinous fibers, a deodorant product, or a scenting product.

19. A makeup composition according to claim 18, additionally comprising a coloring material.

20. A composition according to claim 18, additionally comprising at least one ingredient chosen from preservatives, antioxidants, fragrances, surfactants, and mixtures thereof.

21. A process for producing a mattifying effect on keratinous materials comprising applying on the keratinous materials a composition, said process comprising introducing into the composition, as a thickener, particles of an at least partially crosslinked elastomeric solid organopolysiloxane in suspension in an aqueous phase, wherein said particles are present in an amount effective to produce a mattifying effect.

22. A process according to claim 21, wherein the at least partially crosslinked elastomeric solid organopolysiloxane particles, of at least (i) one organopolysiloxane having at least two vinyl groups in the α- and ω-positions of the silicone chain per molecule, and (ii) one organopolysiloxane having at least one hydrogen atom bonded to a silicon atom per molecule.

23. A process according to claim 22, wherein the suspension of organopolysiloxane particles is obtained by:
   (a) mixing the organopolysiloxane (i) and the organopolysiloxane (ii);
   (b) adding the aqueous phase comprising an emulsifier to the mixture obtained in (a);
   (c) emulsifying the aqueous phase and the mixture to obtain an emulsion;
   (d) adding hot water to the emulsion of (c); and
   (e) polymerizing the organopolysiloxane (i) and the organopolysiloxane (ii) as an emulsion in the presence of a platinum catalyst.

24. A process according to claim 22, wherein the organopolysiloxane (i) is chosen from polydimethylsiloxanes.

25. A process according to claim 24, wherein the organopolysiloxane (i) is an α,ω-dimethylvinylpolydimethylsiloxane.

26. A composition according to claim 17, wherein said cosmetic or dermatological active principle is glycerol.

* * * * *